United States Patent
Javdani et al.

(10) Patent No.: US 7,285,678 B2
(45) Date of Patent: Oct. 23, 2007

(54) PURIFICATION OF 2-NITRO-4-METHYLSULPHONYLBENZOIC ACID

(75) Inventors: Kambiz Javdani, Bucks, AL (US); Gilbert Rodriguez, Bucks, AL (US); James Peter Muxworthy, Huddersfield (GB)

(73) Assignee: Syngenta Limited (GB)

( * ) Notice: Subject to any disclaimer, the term of this patent is extended or adjusted under 35 U.S.C. 154(b) by 328 days.

(21) Appl. No.: 10/472,962

(22) PCT Filed: Mar. 25, 2002

(86) PCT No.: PCT/GB02/01433

§ 371 (c)(1), (2), (4) Date: Apr. 9, 2004

(87) PCT Pub. No.: WO02/076934

PCT Pub. Date: Oct. 3, 2002

(65) Prior Publication Data

US 2004/0171872 A1    Sep. 2, 2004

Related U.S. Application Data

(60) Provisional application No. 60/275,061, filed on Mar. 26, 2001.

(51) Int. Cl.
*C07C 315/06*    (2006.01)

(52) U.S. Cl. ...................... 562/429; 504/348

(58) Field of Classification Search ............. None
See application file for complete search history.

(56) References Cited

U.S. PATENT DOCUMENTS

| 5,006,158 A |   | 4/1991 | Carter et al. |
| 5,055,605 A | * | 10/1991 | Ludvik ............... 560/11 |
| 5,424,481 A |   | 6/1995 | Hagen |
| 6,218,579 B1 | * | 4/2001 | Jones et al. .......... 568/309 |

FOREIGN PATENT DOCUMENTS

WO    90 06301    6/1990

* cited by examiner

*Primary Examiner*—Johann R. Richter
*Assistant Examiner*—Valenrod Yevgeny
(74) *Attorney, Agent, or Firm*—William A. Teoli, Jr.

(57) ABSTRACT

A method for removing impurities from 2-nitro-4-methylsulfonylbenzoic acid which comprises at least two of the following steps, in any order, (a) dissolving 2-nitro-4-methylsulfonylbenzoic acid in water at a pH of about 2 to 10, followed by filtration; (b) contacting an aqueous solution of 2-nitro-4-methylsulfonylberizoic acid with activated carbon at a pH of about 2 to 10; (c) treating an aqueous solution of 2-nitro-4-methylsulfonylbenzoic acid with sufficient base to hydrolyze undesired nitro and dinitro substituted impurities; followed by maintaining the resulting aqueous solution comprising 2-nitro-4-methylsulfonylbenzoic acid at a temperature of up to about 95° C., and adjusting the pH of said solution to about a pH which is sufficient to effect crystallization of 2-nitro-4-methylsulfonylbenzoic acid upon cooling.

8 Claims, No Drawings

PURIFICATION OF 2-NITRO-4-METHYLSULPHONYLBENZOIC ACID this application is a 371 of PCT/GB02/01433 issued Mar. 25, 2002 which claims benefit of Ser. No. 60/275,061 issued Mar. 26, 2001.

The present invention relates to a method for preparing high purity 2-nitro-4-methylsulfonylbenzoic acid, to purified 2-nitro-4-methylsulfonylbenzoic acid from the method, to a process for making mesotrione using the purification method followed by further steps, and to mesotrione produced by this process.

Mesotrione (2-(4-methylsulfonyl-2-nitrobenzoyl)cyclohexane-1,3-dione) is a triketone compound useful as a corn herbicide for pre- and post-emergence control of grass and broadleaf weeds:

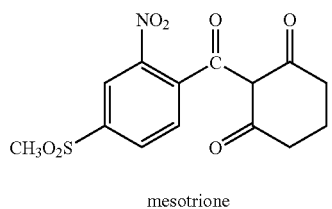

mesotrione

Mesotrione can be manufactured by first reacting 2-nitro-4-methylsulfonylbenzoic acid (NMSBA);

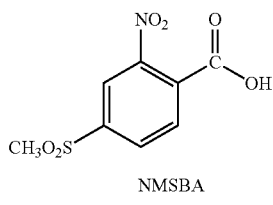

NMSBA with phosgene in the presence of an organic solvent to provide the corresponding acid chloride, i.e.,

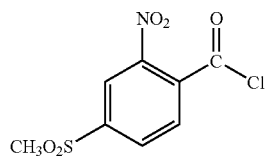

The acid chloride intermediate can then be reacted with 1,3-cyclohexanedione in the presence of a cyanide catalyst and triethylamine to form crude Mesotrione. The solvents can be removed via distillation and the Mesotrione precipitated from the remaining reaction mixture through a series of pH adjustment steps and isolated by filtration or centrifugation.

We have found that mesotrione made by this process can give a positive Ames test result. Surprisingly, we have discovered that this is not an inherent property of mesotrione, nor is it the result of by-products from the reaction outlined above, but in fact results from impurities in the NMSBA starting material. In an effort to overcome this problem and to provide Mesotrione product that exhibits a negative Ames test response, it would be desirable to develop a method for purifying the starting material NMSBA, thereby removing these impurities.

Accordingly, the present invention provides a method for removing impurities from 2-nitro-4-methylsulfonylbenzoic acid, which comprises at least two of the following steps, in any order, (a) dissolving 2-nitro-4-methylsulfonylbenzoic acid in water at a pH of about 2 to 10, followed by filtration;

(b) contacting an aqueous solution of 2-nitro-4-methylsulfonylbenzoic acid with activated carbon at a pH of about 2 to 10;

(c) treating an aqueous solution of 2-nitro-4-methylsulfonylbenzoic acid with sufficient base to hydrolyze undesired nitro and dinitro substituted impurities;

followed by maintaining the resulting aqueous solution comprising 2-nitro-4-methylsulfonylbenzoic acid at a temperature of up to about 95° C., and adjusting the pH of said solution to a pH which is sufficient to effect crystallization of 2-nitro-4-methylsulfonylbenzoic acid upon cooling. Preferably, the pH is adjusted to about 1 prior to cooling and crystallization.

By means of the invention, it is possible to remove impurities typically found in 2-nitro-4-methylsulfonylbenzoic acid which, we have discovered, tend to give a positive Ames test result in the final Mesotrione product.

To maintain the temperature of the resulting solution comprising 2-nitro-4-methylsulfonylbenzoic acid, typically said solution is heated; however, it is possible that the reaction will be at a sufficient temperature so that heating will not be required. The temperature is typically maintained between about ambient and about 95° C., preferably between about 85° C. and about 95° C.

In the method of the invention it is preferred wherein steps (a) and (b) are utilized, wherein steps (a) and (c) are utilized, wherein steps (b) and (c) are utilized, wherein steps (a), (b) and (c) are utilized, or especially wherein steps (a), (b) and (c) are utilized in order.

The method of the invention preferably further comprises the step of washing said crystalline 2-nitro-4-methylsulfonylbenzoic acid with solvent, and optionally drying said crystalline 2-nitro-4-methylsulfonylbenzoic acid.

It is also preferred wherein in step (a) the pH is adjusted to about 3 to 7.

In step (a), the base is preferably selected from the group consisting of potassium hydroxide, calcium hydroxide, ammonium hydroxide, sodium carbonate, and sodium bicarbonate.

It is further preferred wherein in step (b) the activated carbon is in the form of a powder or granule. It is also preferred wherein in step (b), the aqueous solution of 2-nitro-4-methylsulfonylbenzoic acid is passed through a column packed with activated carbon.

In a preferred embodiment, NMSBA solids are dissolved in water at a pH greater than 2 and filtered to remove any insoluble material. The resulting solution is contacted with powdered activated carbon at a pH of about 3 to 8 to remove phenolic, nitro, and nitrophenolic impurities. After further filtration, the resulting solution is further treated under alkaline conditions to hydrolyze nitro and dinitro analogue impurities of NMSBA which may be present as a consequence of the synthetic methodologies leading up to NMSBA. The solution is heated, preferably to about 90-95° C., the pH is adjusted to about 1 with an organic/inorganic acids such as orthophosphoric, oxalic, formic, malic, muriatic, nitric, sulfuric but preferably sulfuric acid and allowed to cool to room temperature. The resulting crystalline NMSBA can be filtered, washed and dried.

According to the present invention there is also provided purified NMSBA produced or producible by the process.

According to the present invention there is also provided a process for producing mesotrione, which comprises removing impurities from NMSBA by the process described above and then converting the resulting purified NMSBA to mesotrione. On known method to do this is to react the NMSBA with 1,3-cyclohexanedione so as to produce mesotrione. Suitable general processes are described, for example in EP 805 792, EP 805 791 and U.S. Pat. No. 6,218,579. Generally, the NMSBA will not react directly with the dione at an acceptable rate, and so the NMSBA is first converted to a more reactive derivative, such as an acid halide or an anhydride. One such route is to convert the NMSBA to the corresponding acid chloride using a chloride source such as thionyl chloride or preferably phosgene, and then react this acid chloride with 1,3-cyclohexanedione so as to produce mesotrione. The reaction of the acid chloride and cyclohexanone can, for example be carried out in the presence of a cyanide catalyst and triethylamine, although other processes are also known. In such processes, typically, the solvents are removed via distillation and the Mesotrione is precipitated from the remaining reaction mixture through a series of pH adjustment steps and isolated by filtration or centrifugation. According to the present invention there is also provided a method of avoiding the production of Ames-positive mesotrione by using the above process to purify NMSBA which is then used to make the mesotrione as described. According to the present invention there is also provided Ames-negative mesotrione produced or producable by this process.

The following examples are to illustrate the invention but should not be interpreted as a limitation thereon.

EXAMPLE 1

This example illustrates a "one pot" purification process of 2-nitro-4-methanesulfonylbenzoic acid.

A 1L round bottom glass reactor equipped with an agitator, paddle, thermometer, heating mantle, condenser, pH electrode and 100 ml dropping funnel, was charged with 360 ml water followed by 100 g NMSBA powder to form a slurry under moderate agitation. The mixture was charged 56 g of caustic at a rate of about 2 mL per minute to dissolve the solids. Allowed the mixture to agitate for 30 minutes until all the solids are dissolved to form milky white mixture at pH 3.65.

The resulting mixture was filtered through a #4 Whatman filter paper in a Buchner funnel under 50 mm Hg vacuum to give a clean light amber mother liquor. The mother liquor was filtered again through a #5 Whatman filter paper in a Buchner funnel under vacuum. The mother liquor was returned to the reactor and 10 g of Calgon activated carbon 2PG 10×40 was added. The mixture was stirred moderately to prevent carbon attrition for 2 hours at 30° C. The carbon mixture was filtered at pH 4.0 through a #4 and #5 Whatman filters, respectively to remove spent carbon and residual carbon fines.

The clear mother liquor was returned to the 1 litre reactor and charged with 7.1 g of 25% NaOH to raise pH from 4.1 to 13.0. The darker alkaline mixture was allowed to agitate moderately at 30° C. for 1.5 hours to hydrolyze the overnitrated NMSBA analog impurities.

The mixture was acidified at ambient temperature by charging 5.1 grams of 40% $H_2SO_4$ from pH 13 to pH 3.6 and started heating to 90° C. When the temperature was at 90° C. the mixture was acidified further from pH 3.6 to pH 0.8. The solution was cooled slowly to 60° C. and then under an ice bath to ambient temperature, 25° C.

The resulting slurry was filtered through a Buchner funnel with #4 Whatman filter paper. The cake was washed twice with 300 mL of tap water and dewatered. About 112.5 g of wet solids were isolated from the mixture. The solids were then dried in a vacuum oven at 60° C. overnight to result in 90 g of light amber powder. The purification yield was 94.7%. The material was converted to Mesotrione which exhibited a negative Ames test.

EXAMPLE 2

One Pot Integrated Process—Effect of Carbon

This example illustrates the "one pot" integrated process to purify 2-nitro-4-methanesulfonylbenzoic acid (NMSBA).

To a 2L round bottom glass reactor with agitator paddle, heating mantle condenser, thermometer was charged 902 ml of water and 100 grams of crude NMSBA to form a slurry. To the slurry was charged 61 g of 25% NaOH solution to pH 3.7. The mixture was filtered through a Buchner funnel with #4 Whatman filter paper and a white residue was collected on the filter paper. The filtrate was filtered again through a #5 Whatman filter paper. The clear mother liquor was split in two equal fractions. To one fraction was charged 5 g of activated carbon and none to the other.

The fraction with carbon was stirred for 2 hours at ambient temperature at pH 3.7 and then filtered thought a #4 and #5 Whatman filter paper in Buchner funnel. The mother liquor was returned to the reactor and charged 90 g of 25% NaOH solution to pH 13 and raised the temperature to 90° C. for a few minutes. To the hot mixture was charged 175 ml of 40% sulfuric acid to pH 0.8 and cooled slowly to crystallize the mixture. The slurry was filtered and the solids washed and dried.

The pH of the second fraction (no carbon) was raised from 3.7 to 13 within 92 grams of 25% NaOH solution and heated to 90° C. for a few minutes. To the hot mixture was added 180 g of 40% sulfuric acid to lower the pH from pH 13 to 0.8. The mixture was then cooled slowly to crystallize the product. The NMSBA solids for the fractions were isolated by filtration through a Buchner funnel with #4 Whatman filter paper. The filter cake was washed 2×100 of tap water and dewatered. The wet cake was dried in a vacuum oven at 60° C. for 4 hrs. The fraction with carbon afforded 43.2 grams of dry NMSBA and the fraction without carbon 44.3 grams. These represent a recovery yield of 92 and 94% respectively in relation to crude NMSBA. The purified NMSBA materials from the fractions were converted to Mesotrione product and tested for activity in the Ames test. These resulted with an Ames negative response.

EXAMPLE 3

This example illustrates purification process of 2-nitro-4-methanesulfonylbenzoic acid by the procedure described in Example 2. This was done under various NMSBA product loading in relation to initial charge of 20, 30, and 50% using the following stoichiometry:

| NMSBA Loading | | | |
|---|---|---|---|
| | Example | | |
| | A | B | C |
| Materials: | | | |
| | 20% | 30% | 40% |
| Crude NMSBA (90%), grams | 35 | 90 | 110 |
| Tap Water | 142 | 210 | 267 |
| 25% NaOH, grams (pH 3.5) | 22 | 78 | 70.4 |
| 25% NaOH, grams (pH 13) | 6.2 | | 70 |
| 40% $H_2SO_4$, grams | 29 | 183 | 214 |
| Activated Carbon, grams (Calgon 10 × 40) | 4 | 9.0 | 10.7 |

The resulting batches gave 28, 74 and 90 g of NMSBA product for the 20, 30 and 40% solids loading. The NMSBA was analyzed and showed assays ranging from 99-100% by HPLC area % without detection of outstanding impurities. The technical yields for batches ranging from 89 to 91% in relation to the starting crude NMSBA. This material was converted to Mesotrione which exhibited a negative Ames test.

EXAMPLE 4

Double Isolation Process

This example illustrates the purification of 2-nitro-4-methylsulfonylbenzoic acid by a "double" isolation process.

$1^{st}$ Isolation:

The 2-nitro-4-methylsulfonylbenzoic acid crude material was first treated by the procedure described in Example 1, with the processing steps consisting of dissolution, filtration of insoluble impurities, hydrolysis, crystallization, isolation and drying.

$2^{nd}$ Isolation:

To a 5 litre round bottom agitated reactor equipped with thermometer, heating mantle, condenser, pH electrode and 500 ml dropping funnel, 206 g of 2-nitro-4-methylsulfonylbenzoic acid solids and 1800 g of water were added to form a slurry. Next, 125 g of 25% NaOH solution was added via dropping funnel to dissolve the solids at pH 3.5. The resulting mixture was filtered twice through a Buchner funnel equipped with 2.5 micron Whatman #5 filter paper to result in 2172 grams of clear filtrate with pH of 3.5.

The resulting sodium salt solution of the 2-nitro-4-methylsulfonylbenzoic acid was split in two equal fractions of 1086 g each. The Fraction (A) was charged with 33 g of activated carbon, heated to 90° C. by charging 210 ml of 40% sulfuric acid solution slowly via a dropping funnel to pH 0.9. At this pH the mixture formed a slurry with large crystals.

The Fraction (B) mixture was contacted with 10 g of activated carbon for one hour at ambient temperature under moderate agitation and allowed to sit overnight before removing spent carbon by filtration through a 40 micron fritted glass funnel. The filtrate was crystallized at ambient temperature by charging 195 mL of 40% sulfuric acid solution slowly via dropping funnel at pH 0.89. At this pH the mixture formed a slurry with slightly smaller crystals than fraction (A).

The resulting slurries from (A) and (B) fractions were filtered separately through a Buchner funnel equipped with #4 Whatman filter paper. The wet cake from each filtration was washed twice with 300 ml of tap water, dewatered and dried in a vacuum oven overnight at 40° C. The (A) and (B) fractions gave 90 and 88 g of purified 2-nitro-4-methylsulfonylbenzoic acid, respectively. These fractions were converted to Mesotrione which exhibited negative Ames test response.

EXAMPLE 5

The sodium salt solution of NMSBA that has already been subjected to the first isolation as described in Example 1 is prepared by charging 2,700 grams of water and 300 g of NMSBA to a 5l round bottom glass agitated reactor at ambient temperature to form a slurry, followed by addition of 187 g of 25% NaOH solution via dropping funnel to pH of 3.2±0.1 to form a clear mixture. Agitation is continued at a moderate rate at ambient temperature (20-25° C.). This solution is filtered (350 g of this solution) at pH 3.2 through a Buchner funnel equipped with #5 Whatman filter paper (2.5 micron) with vacuum at ambient temperature 20-25° C. The mother liquor is then charged (pH 3.2) to a 1L reactor equipped with an agitator with Teflon® paddle, thermometer, $I^2R$ Therm-o-Watch controller, heating mantle and condenser. The mixture is heated at 90° C. for 5-10 minutes under moderate agitation.

To this mixture is added 10.0 g of activated carbon to the hot mixture and agitate for 1 hr at 90° C. (optional). The agitation is then stopped and the mixture is filtered through a medium porosity Kimax fritted glass funnel at 90° C. with vacuum to remove the carbon. The carbon is rinsed twice with 25 ml of tap water.

The filtrate is then returned to the reactor and the temperature is raised to 90° C. To the reactor is charged 40% $H_2SO_4$ solution slowly to adjust pH of the mixture from 3.2 to 1.0±0.2 followed by cooling slowly to 60° C. NMSBA crystals should start forming at about 85° C. Cooling is continued under a cold water or ice bath from 60° C. to 20-25° C.

The slurry is then filtered through a Buchner Funnel with #4 Whatman filter paper and the wet solid cake is washed twice with 100 ml of tap water. The solids are then dried in a vacuum oven at 60° C. for 8 hours.

The invention claimed is:

1. A method for removing impurities from 2-nitro-4-methylsulfonylbenzoic acid which comprises the following steps,
   (a) dissolving 2-nitro-4-methylsulfonylbenzoic acid in water at a pH of about 2 to 10, followed by filtration;
   (b) contacting an aqueous solution of 2-nitro-4-methylsulfonylbenzoic acid with activated carbon at a pH of about 2 to 10;
   (c) treating an aqueous solution of 2-nitro-4-methylsulfonylbenzoic acid with sufficient base to hydrolyze undesired nitro and dinitro substituted impurities;
   followed by maintaining the resulting aqueous solution comprising 2-nitro-4-methylsulfonylbenzoic acid at a temperature of up to about 95° C., and adjusting the pH of said solution to about a pH which is sufficient to effect crystallization of 2-nitro-4-methylsulfonylbenzoic acid upon cooling;
      wherein in said method, the method steps (a) and (b) are utilized, in any order; or wherein steps (b) and (c) are utilized, in any order; or wherein steps (a), (b) and (c) are utilized, in any order; or wherein steps (a), (b) and (c) are utilized in order.

2. The method of claim 1, further comprising the step of washing said crystalline 2-nitro-4-methylsulfonylbenzoic acid with solvent, and optionally drying said crystalline 2-nitro-4-methylsulfonylbenzoic acid.

3. The method of claim 1, wherein in step (a), the base is selected from the group consisting of potassium hydroxide, calcium hydroxide, ammonium hydroxide, sodium carbonate, and sodium bicarbonate.

4. The method of claim 1, wherein in step (b), the activated carbon is in the form of a powder or granule.

5. The method of claim 1, wherein in step (b), the aqueous solution of 2-nitro-4-methylsulfonylbenzoic acid is passed through a column packed with activated carbon.

6. A process for making mesotrione comprising purifying 2-nitro-4-methylsulfonylbenzoic acid according to the method of claim 1, and converting this purified 2-nitro-4-methylsulfonylbenzoic acid to mesotrione.

7. The process of claim 6, in which the purified 2-nitro-4-methylsulfonylbenzoic acid is converted to mesotrione by reaction with 1,3-cyclohexanedione.

8. The process of claim 7, in which the purified 2-nitro-4-methylsulfonylbenzoic acid is first converted to the corresponding acid chloride which is then reacted with 1,3-cyclohexanedione.

* * * * *